United States Patent
Caren et al.

(10) Patent No.: US 7,147,362 B2
(45) Date of Patent: Dec. 12, 2006

(54) METHOD OF MIXING BY INTERMITTENT CENTRIFUGAL FORCE

(75) Inventors: Michael P. Caren, Palo Alto, CA (US); Carol T. Schembri, San Mate, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 231 days.

(21) Appl. No.: 10/687,276

(22) Filed: Oct. 15, 2003

(65) Prior Publication Data

US 2005/0083781 A1    Apr. 21, 2005

(51) Int. Cl.
*B01F 5/06*    (2006.01)

(52) U.S. Cl. .................. 366/135; 366/150.1; 366/228; 366/235; 366/DIG. 1; 366/DIG. 3; 435/6; 435/287.2; 435/303.3; 422/209

(58) Field of Classification Search ................ 366/131, 366/135, 150.1, 213, 214, 220, 225, 228, 366/235, DIG. 1, DIG. 3; 435/4, 6, 287.2, 435/303.3; 422/72, 209
See application file for complete search history.

(56) References Cited

U.S. PATENT DOCUMENTS

| | | | |
|---|---|---|---|
| 3,744,975 A * | 7/1973 | Mailen | ........................ 422/72 |
| 4,426,451 A | 1/1984 | Columbus | |
| 5,104,813 A | 4/1992 | Besemer et al. | |
| 5,230,866 A | 7/1993 | Shartle et al. | |
| 5,693,233 A | 12/1997 | Schembri | |
| 5,804,384 A | 9/1998 | Muller et al. | |
| 5,837,832 A * | 11/1998 | Chee et al. | ................ 536/22.1 |
| 5,912,134 A | 6/1999 | Shartle | |
| 6,103,199 A | 8/2000 | Bjornson et al. | |
| 6,296,020 B1 | 10/2001 | McNeely et al. | |
| 6,319,469 B1 * | 11/2001 | Mian et al. | .................. 422/64 |
| 6,395,232 B1 | 5/2002 | McBride | |
| 6,448,090 B1 | 9/2002 | McBride | |
| 6,451,188 B1 | 9/2002 | Sundberg et al. | |
| 6,458,599 B1 | 10/2002 | Huang | |
| 6,488,827 B1 | 12/2002 | Shartle | |
| 6,521,182 B1 | 2/2003 | Shartle et al. | |
| 6,527,432 B1 * | 3/2003 | Kellogg et al. | .......... 366/182.1 |
| 2002/0097632 A1 * | 7/2002 | Kellogg et al. | ............. 366/220 |
| 2002/0177159 A1 * | 11/2002 | Bedilion et al. | ................ 435/6 |
| 2005/0084866 A1 * | 4/2005 | Caren et al. | ................... 435/6 |

FOREIGN PATENT DOCUMENTS

WO    WO 99/42605    8/1999

* cited by examiner

*Primary Examiner*—David Sorkin (57) ABSTRACT

An apparatus for mixing fluids comprises a housing having at least a portion of its interior, for example, a channel, with capillary dimensions and at least one structural member in the interior adjacent an end of the channel. The dimensions of and placement of the structural member are sufficient such that intermittent application of centrifugal force to the interior of the housing causes movement of the fluid therein. The housing may comprise a mixing chamber or area that is in fluid communication with the interior. The apparatus may comprise a mechanism adapted to generate centrifugal force within the housing to cause movement of fluid in the interior of the housing without exit of fluid therefrom.

26 Claims, 2 Drawing Sheets

METHOD OF MIXING BY INTERMITTENT CENTRIFUGAL FORCE

BACKGROUND OF THE INVENTION

The present invention relates to apparatus and methods for conducting chemical and biological analyses using linear arrays. More particularly, the invention relates to apparatus and methods for carrying out mixing operations in hybridization reactions using linear microarrays. The invention has utility in fields relating to biology, chemistry and biochemistry.

Determining the nucleotide sequences and expression levels of nucleic acids (DNA and RNA) is critical to understanding the function and control of genes and their relationship, for example, to disease discovery and disease management. Analysis of genetic information plays a crucial role in biological experimentation. This has become especially true with regard to studies directed at understanding the fundamental genetic and environmental factors associated with disease and the effects of potential therapeutic agents on the cell. Such a determination permits the early detection of infectious organisms such as bacteria, viruses, etc.; genetic diseases such as sickle cell anemia; and various cancers. New methods of diagnosis of diseases, such as AIDS, cancer, sickle cell anemia, cystic fibrosis, diabetes, muscular dystrophy, and the like, rely on the detection of mutations present in certain nucleotide sequences. This paradigm shift has lead to an increasing need within the life science industries for more sensitive, more accurate and higher-throughput technologies for performing analysis on genetic material obtained from a variety of biological sources.

Unique or misexpressed nucleotide sequences in a polynucleotide can be detected by hybridization with a nucleotide multimer, or oligonucleotide, probe. Hybridization reactions between surface-bound probes and target molecules in solution may be used to detect the presence of particular biopolymers. Hybridization is based on complementary base pairing. When complementary single stranded nucleic acids are incubated together, the complementary base sequences pair to form double stranded hybrid molecules. These techniques rely upon the inherent ability of nucleic acids to form duplexes via hydrogen bonding according to Watson-Crick base-pairing rules. The ability of single stranded deoxyribonucleic acid (ssDNA) or ribonucleic acid (RNA) to form a hydrogen bonded structure with a complementary nucleic acid sequence has been employed as an analytical tool in molecular biology research. An oligonucleotide probe employed in the detection is selected with a nucleotide sequence complementary, usually exactly complementary, to the nucleotide sequence in the target nucleic acid. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present.

Such reactions form the basis for many of the methods and devices used in the field of genomics to probe nucleic acid sequences for novel genes, gene fragments, gene variants and mutations. The ability to clone and synthesize nucleotide sequences has led to the development of a number of techniques for disease diagnosis and genetic analysis. Genetic analysis, including correlation of genotypes and phenotypes, contributes to the information necessary for elucidating metabolic pathways, for understanding biological functions, and for revealing changes in genes that confer disease. Many of these techniques generally involve hybridization between a target nucleotide sequence and a complementary probe, offering a convenient and reliable means for the isolation, identification, and analysis of nucleotides. The surface-bound probes may be oligonucleotides, peptides, polypeptides, proteins, antibodies or other molecules capable of reacting with target molecules in solution.

Direct detection of labeled target nucleic acid hybridized to surface-bound polynucleotide probes is particularly advantageous if the surface contains a mosaic of different probes that are individually localized to discrete, known areas of the surface. Such ordered arrays of probes are commonly referred to as "biochip" arrays. Biochip arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

In one approach, cell matter is lysed, to release its DNA as fragments, which are then separated out by electrophoresis or other means, and then tagged with a fluorescent or other label. The resulting DNA mix is exposed to an array of oligonucleotide probes, whereupon selective attachment to matching probe sites takes place. The array is then washed and imaged so as to reveal for analysis and interpretation the sites where attachment occurred.

One typical method involves hybridization with probe nucleotide sequences immobilized in an array on a substrate having a surface area of typically less than a few square centimeters. The substrate may be glass, fused silica, silicon, plastic or other material; typically, it is a glass slide, which has been treated to facilitate attachment of the probes. The mobile phase, containing reactants that react with the attached probes, is placed in contact with the substrate, covered with another slide, and placed in an environmentally controlled chamber such as an incubator. Normally, the reactant targets in the mobile phase diffuse through the liquid to the interface where the complementary probes are immobilized, and a reaction, such as a hybridization reaction, then occurs. The mobile phase targets may be labeled with a detectable tag, such as a fluorescent tag, or chemiluminescent tag, or radioactive label, so that the reaction can be detected. The location of the signal in the array provides the target identification. The hybridization reaction typically takes place over a time period of seconds up to many hours.

Biochip arrays have become an increasingly important tool in the biotechnology industry and related fields. These binding agent arrays, in which a plurality of binding agents are synthesized on or deposited onto a substrate in the form of an array or pattern, find use in a variety of applications, including gene expression analysis, drug screening, nucleic acid sequencing, mutation analysis, and the like. Substrate-bound biopolymer arrays, particularly oligonucleotide, DNA and RNA arrays, may be used in screening studies for determination of binding affinity and in diagnostic applications, e.g., to detect the presence of a nucleic acid containing a specific, known oligonucleotide sequence.

The pattern of binding by target molecules to biopolymer probe spots on the biochip forms a pattern on the surface of the biochip and provides desired information about the sample. Hybridization patterns on biochip arrays are typically read by optical means, although other methods may also be used. For example, laser light in the Agilent Technologies Inc. GeneArray Scanner excites fluorescent molecules incorporated into the nucleic acid probes on a biochip, generating a signal only in those spots on the biochip that have a target molecule bound to a probe molecule, thus generating an optical hybridization pattern. This pattern may be digitally scanned for computer analysis. Such patterns can be used to generate data for biological assays such as the identification of drug targets, single-nucleotide polymorphism mapping, monitoring samples from patients to track their response to treatment, and assess the efficacy of new treatments.

One type of linear array is a one-dimensional array of features bound in a non-diffusive manner to a surface, which may be located on the inside of an enclosed microchannel. The order of the features identifies each feature, which allows selective identification of target molecules. One such linear array is disclosed in U.S. Pat. No. 5,804,384 (Muller, et al.). The devices of Muller, et al., consist of a tube containing a linear array of specific binding elements that each have capture probes specific for a target analyte.

Inadequate mixing is a particular problem in chemical and biological assays where very small samples of chemical, biochemical, or biological fluids are typically involved. Inhomogeneous solutions resulting from inadequate mixing can lead to poor hybridization kinetics, low efficiency, low sensitivity, and low yield. With inadequate mixing, diffusion becomes the only means of transporting the reactants in the mobile phase to the interface or surface containing the immobilized reactants. In such a case, the mobile phase can become depleted of reactants near the substrate as mobile molecules become bound to the immobile phase.

Methods for mixing relatively large volumes of fluids may utilize conventional mixing devices that mix the fluids by shaking the container, by a rapid mechanical up and down motion, or by the use of a rocking motion that tilts the container filled with the fluids in a back and forth motion. The conventional mixing methods normally cannot be utilized for small volumes of fluid such as thin films of fluids in capillary chambers because the capillary strength of the containment system often significantly exceeds the forces generated by shaking or rocking, thereby preventing or minimizing fluid motion in the film. This is because most or all of the fluid is so close to the walls of the chamber that there is virtually no bulk phase so that surface interactions predominate.

There remains a need in the art for efficient and effective methods and apparatus for mixing fluids in small chambers such as capillary chambers in which linear arrays are housed.

SUMMARY OF THE INVENTION

One embodiment of the present invention is an apparatus for mixing fluids. The apparatus comprises a housing having at least a portion of its interior, for example, a channel, with capillary dimensions and at least one structural member in the interior adjacent an end of the channel. The dimensions of and placement of the structural member are sufficient such that intermittent application of centrifugal force to the interior of the housing causes movement of the fluid therein. The housing may comprise a mixing chamber or area that is in fluid communication with the interior. The apparatus may comprise a mechanism for generating centrifugal force, e.g. a rotatable support for rotating the housing to produce the centrifugal force. The mechanism is adapted to produce intermittent centrifugal force to cause movement of fluid in the interior of the housing without exit of fluid therefrom. The apparatus may optionally comprise a fluid dispensing device. The interior of the apparatus may comprise a linear array of features for conducting chemical reactions and the apparatus may be employed to conduct such reactions.

Another embodiment of the present invention is an apparatus for conducting hybridization reactions. The apparatus comprises a housing having an interior with capillary dimensions, a structural member in the interior adjacent an end of the housing, and a mechanism adapted to generate centrifugal force in the interior of the housing. The interior comprises a linear microarray of biopolymers for conducting hybridization reactions. The interior may also comprise a mixing area adjacent said linear microarray. The dimensions of and placement of the structural member are sufficient such that intermittent application of centrifugal force to the interior causes reciprocal movement of the fluid in the interior between said linear microarray and said mixing area. Optionally, the apparatus may comprise a fluid dispensing device.

Another embodiment of the present invention is a method for mixing a fluid. The method comprises introducing a fluid into a housing of an apparatus as described above and generating intermittent centrifugal force to cause movement of the fluid but insufficient to cause the fluid to exit the housing.

Another embodiment of the present invention is a method for conducting chemical reactions. The method comprises introducing a sample into a housing of an apparatus as described above and incubating the sample in the housing under conditions for carrying out the chemical reactions. During the incubation intermittent centrifugal force is generated to cause reciprocal movement of the fluid in the interior of the housing between the linear array and the mixing area but insufficient to cause the fluid to exit the housing.

Another embodiment of the present invention is a method for conducting hybridization reactions. A sample is introduced into a housing comprising a linear microarray of features for hybridizing to analytes in the sample and a mixing area. The housing has internal capillary dimensions and a structural member in the interior adjacent an end of the housing. The dimensions of and placement of the structural member are sufficient such that intermittent application of centrifugal force to the interior causes motion of the fluid in the housing. The sample is incubated in the housing under conditions for carrying out the hybridization reactions. During the incubation intermittent centrifugal force is generated to cause reciprocal movement of the fluid between the linear array and the mixing area but insufficient to cause the fluid to exit the housing. Rotating the housing may generate the intermittent centrifugal force. Optionally, the centrifugal force may be increased to a level sufficient to cause the fluid to exit the interior. A wash fluid may be introduced into the housing and intermittent centrifugal force may be generated sufficient to cause movement of the wash fluid but insufficient to cause the wash fluid to exit the housing. Optionally, the centrifugal force may be increased to a level sufficient to cause the fluid to exit the interior.

BRIEF DESCRIPTION OF THE DRAWINGS

The following figures are included to better illustrate the embodiments of the devices and techniques of the present invention. The figures are not to scale and some parts of the figures may be exaggerated for the purpose of illustrating certain aspects or embodiments of the present invention.

DETAILED DESCRIPTION OF SPECIFIC EMBODIMENTS

The present invention utilizes a capillary valve and centrifugal force to induce mixing in fluids. In one embodiment the capillary valve may comprise small structural members, which essentially act as a capillary leash, i.e., a way of controlling the movement of fluid in a capillary environment. Centrifugal force may be employed to move fluid in a capillary channel within a housing while retaining the fluid within the channel or to move the fluid to a mixing area and back to the channel. To remove fluid from the channel, the centrifugal force is increased to a level to overcome the capillary forces within the channel. The centrifugal force may be applied to the channel by rotating the channel.

The present invention provides a multi-function valve that acts as a leash to control movement of the fluid within a capillary environment and to control exit of fluid from the capillary environment. The valve may be fabricated at the same time as the fabrication of the capillary housing. The functions of the valve may be controlled by the same parameter, i.e., the rotational speed of the capillary housing. A combination of the multi-function valve and centrifugal force may be employed to mix fluids within, and to control exit of fluids from, the capillary housing. The apparatus of the present invention is easy to automate and to fabricate.

The term "mixing" includes mixing of multi-component systems as well as solutions that are inhomogeneous due to depletion of certain components over other components present in a complex mixture of components. For example, a sample comprising a plurality of analytes applied to a linear array experiences localized depletion of certain analytes as the sample contacts the linear array thus resulting in an inhomogeneous solution. Mixing as used herein includes agitation of inhomogeneous solutions or samples to overcome this type of inhomogeneity.

The phrase "adapted to" or "adapted for" is used herein with respect to components of the present apparatus. The components of the present apparatus are adapted to perform a specified function by a combination of hardware and software. This includes the structure of the particular component and may also include a microprocessor, embedded real-time software and I/O interface electronics to control the sequence of operations of the invention.

The housing is any enclosure in which at least a portion of the interior has capillary dimensions. The housing may comprise a microchannel. In one approach, the microchannel is part of a microfluidic system. Microfluidic systems have been developed for performing chemical, clinical, and environmental analysis of chemical and biological specimens. The term microfluidic system refers to a system or device having a network of chambers connected by channels, in which the channels have microscale features, that is, features too small to examine with the unaided eye. The channel often has a capillary dimension, i.e., a cross-sectional area that provides for capillary flow through the channel. At least one of the cross-sectional dimensions, e.g., width, height, diameter, is at least about 1 µm, at least about 10 µm, and is typically no more than about 500 µm, typically no more than about 200 µm. Channels of capillary dimension typically have an inside bore diameter (ID) of from about 1 to about 200 microns, more typically from about 25 to about 100 microns. The term "microfluidic" generally means of or pertaining to fluids and being of a magnitude on the order consistent with capillary dimension. The channel(s) may be part of a microfluidic network or a system of interconnected cavity structures and capillary-size channels configured with a plurality of branches through which fluids may be manipulated and processed. In one simple form, the present apparatus comprise a microchannel in the form of a tube within a housing.

The capillary leash generally comprises one or more structural members in a capillary channel, which may be near an end of a capillary channel. The structural members may be any structure that permits the desired effect of retaining and mixing fluid in the capillary channel at one speed of rotation and releasing the fluid from the capillary channel at another speed of rotation. The structural member may be in or on a wall of the capillary channel or separate therefrom. In general, the structural member changes the capillary dimensions of the capillary in the area of the structure. The change in the capillary dimension may be an increase or a decrease, for example, an increase. The structural member permits fluid in the capillary channel to be maintained in and mixed in the capillary channel at a first predetermined pressure difference across the area of the structure and to break through the area adjacent the structural member when there is a second predetermined pressure difference across the area of the structural member. The structural member may be an indentation or recess in, or protrusion on, a wall of the capillary channel. On the other hand, the structural member may be separate from the wall of the capillary channel and non-movably secured therein. To this end, the separate structural member may be attached to the wall of the capillary channel by means such as adhesives, sonic welding, heat, pressure, spin coating, photolithographic etching and the like. Any adhesive or other means of attachment employed must be compatible with the fluids that will be introduced into the capillary channel during use of the present apparatus. The separate structural member may be secured in the capillary channel by friction fitting and the like. In any event, the separate structural member must be able to withstand the forces applied to the capillary channel and the present device during the course of its use in the methods of the present invention.

The structural member may have any convenient shape such as, for example, circular, oval, rectangular, square, and so forth. Other considerations regarding the structural member relate primarily to capillarity and, thus, pressure and include manufacturability, surface wettability and the like.

The dimensions of the structural member are dependent on the capillary dimensions of the channel comprising the array, the shape of the channel, the length of the channel, the viscosity and/or surface tension of fluid that is to be moved within the capillary housing, the rpm constraints of the motor rotating the linear array, and so forth. For circular capillary channels with interior dimensions of about 10 to about 500 microns, the dimensions of the structural member are about 1 to about 100 microns, about 2 to about 50 microns, about 4 to about 40 microns, about 5 to about 30 microns, about 10 to about 20 microns.

The structural member(s) are generally placed adjacent an end of the capillary channel, which may be an end where fluid ultimately exits the capillary channel. The placement of the structural members is such as to achieve the intermittent movement of fluid between the linear array and the mixing area without fluid exiting the capillary channel. The structural member(s) are placed within about 1 to about 1000 microns, within about 10 to about 500 microns, within about 20 to about 200 microns, within about 50 to about 100 microns, of the end of the capillary channel.

The materials from which the structural members may be fabricated may be naturally occurring or synthetic or modified naturally occurring. The material should be compatible with the fluids that are in contact with the interior of the capillary channel. Thus, the material should not be reactive with or in any way cause deterioration of such fluids. The material may be homogeneous or heterogeneous, that is, the material may comprise a single component or it may comprise multiple components in the form of layers, composites, laminates, blends, photo-defined polymers, and the like. The material may be the same as or different from the material from which the housing is fabricated.

In one approach, the structural member and the capillary housing are formed from the same material. In one approach, the capillary housing and the structural member are manufactured from the same material as an integral system as discussed in more detail below.

Examples of structural members that may be employed in the present apparatus and methods include, by way of illustration and not limitation, those structures described in U.S. Pat. No. 4,426,451 (Columbus), U.S. Pat. No. 5,912,134 (Shartle 1), U.S. Pat. No. 6,488,827 (Shartle 2), U.S. Pat. No. 5,230,866 (Shartle, et al., 1), U.S. Pat. No. 6,521,182 (Shartle, et al., 2), U.S. Pat. No. 6,103,199 (Bjornson, et al.), U.S. Pat. No. 5,693,233 (Schembri), and U.S. Pat. No. 5,104,813 (Besemer, et al.), the relevant disclosures thereof are incorporated herein by reference.

In general, the material for the housing should provide physical support for the chemical compounds that are deposited on an interior surface of the housing or synthesized on an interior surface of the housing in situ from subunits. The materials should be of such a composition that they endure the conditions of a deposition process and/or an in situ synthesis and of any subsequent treatment or handling or processing that may be encountered in the use of a particular array.

Typically, the housing material is transparent or comprises a viewing area that is transparent. By "transparent" is meant that the substrate material permits signal from features on an interior surface of the substrate to pass therethrough without substantial attenuation and also permits any interrogating radiation to pass therethrough without substantial attenuation. By "without substantial attenuation" may include, for example, without a loss of more than about 40% or more typically without a loss of more than about 30%, about 20% or about 10%, of signal. The interrogating radiation and signal may for example be visible, ultraviolet or infrared light. In certain embodiments, such as for example where production of binding pair arrays for use in research and related applications is desired, the materials from which the substrate may be fabricated should ideally exhibit a low level of non-specific binding during chemical reactions such as, e.g., hybridization events. Alternatively, the material may be opaque if the covering forming the top of channel comprising the linear array is removed or opened prior to a scanning for optical signal or if non-optical detection methods are employed such as radiation.

Particular plastics finding use for the housing include, for example, flexible or rigid forms of polyethylene, polypropylene, polytetrafluoroethylene (PTFE), e.g., TEFLON®, polymethylmethacrylate, polycarbonate, polyethylene terephthalate, polystyrene or styrene copolymers, polyurethanes, polyesters, polycarbonates, polyureas, polyamides, polyethyleneamines, polyarylene sulfides, polysiloxanes, polydimethylsiloxanes, polyimides, polyacetates, poly etheretherketone (PEEK), and the like, either used alone or in conjunction with another material or materials. The housing may be rigid or flexible.

Suitable rigid materials may include glass, which term is used to include silica, and include, for example, glass such as glass available as Bioglass, and suitable rigid plastics and resins, and so forth. Rigid plastics include, for example, polymers such as, e.g., poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc., either used by themselves or in conjunction with other materials.

In one exemplary embodiment the structural member is in the form of a photo-defined polymer such as, for example, a polyamide and the like. Other photopolymers suitable for the present invention will be familiar to those skilled in the art in view of the teaching herein.

The structural member may be integral with the interior of the housing of the present device or it may be separate therefrom. The structural member may comprise a single element or multiple elements that cooperate to narrow the passage of the capillary channel. The structural member may take any of a number of geometrical forms depending on the above considerations. Such forms include, for example, cylindrical, rectangular, triangular, and the like.

In one embodiment, the structural member is a pair of rectangular photolithographically defined barriers. These barriers form capillary channels smaller in dimension that the capillary channel housing the linear array and, therefore, act as a capillary leash to hold onto the fluid as centrifugal force is applied to the linear array. Alternatively, a neck in the capillary channel may be formed; the neck is integral with the interior of the capillary channel. The neck serves the same function as the aforementioned pair of barriers.

Microfluidic systems are often fabricated using photolithography, wet chemical etching, and other techniques similar to those employed in the semiconductor industry. The resulting devices can be used to perform a variety of sophisticated chemical and biological analytical techniques.

In one specific embodiment of the present apparatus, the channel is a conduit by which a sample may contact a linear array comprising a plurality of features for conducting chemical reactions. The channels, and thus the linear array, may be straight, curved, serpentine, labyrinth-like or other convenient configuration comprised of separate tubes or part of a monolithic, often planar, substrate. The cross-sectional shape of the channel is not critical and may be circular, ellipsoid, square, rectangular, triangular and the like. The inside of the channel may be coated with a material for strength, for enhancing or reducing electrokinetic flow, for enhancing detection limits and sensitivity, and so forth. Exemplary of coatings are silylation, polyacrylamide (vinyl bound), methylcellulose, polyether, polyvinylpyrrolidone, and polyethylene glycol, polypropylene, Teflon™ (DuPont), Nafion™ (DuPont), and the like may also be used.

The channel may comprise at least one entry port, namely, any site at which a liquid may be introduced into a device having one or more channels. The entry port may be a well or simply the terminus of a channel that opens any place on the device such as at an edge. The channel may comprise at least one port from which fluid exiting the channel may travel to a collection chamber and the like.

The channel or the housing may also comprise a mixing area to which the fluid may move, without exiting the channel, in response to application of centrifugal force to said housing such as by rotation of the housing comprising the channel. As intermittent centrifugal force is applied to the housing, the fluid moves back and forth between the mixing area and the capillary channel. The mixing area may be a portion of the capillary channel or it may be independent thereof but in fluid communication with the capillary channel. The dimensions of the mixing area are dependent on the dimensions of the capillary channel, the dimensions of the structure, the amount of fluid, and so forth. The dimensions of the mixing area for capillary channels are about 10 to about 10,000 microns, about 50 to about 5,000 microns, about 100 to about 2,000 microns, about 500 to about 1,000 microns. The placement of the mixing area is such as to achieve the intermittent movement of fluid between the linear array and the mixing area without fluid exiting the capillary channel. The mixing area is placed within about 10 to about 10,000 microns, about 50 to about 5,000 microns, about 100 to about 2,000 microns, about 500 to about 1,000 microns, of the end of the capillary channel.

Microfluidic devices generally include one or more channels fabricated on or within the devices, for example, within the devices. The devices also can include reservoirs, fluidly connected to the channels, which can be used to introduce materials into the channels to contact a linear array contained in the channel. Microfluidic systems have a number of advantages over conventional chemical or physical laboratory techniques. For example, microfluidic systems are particularly well adapted for analyzing small sample sizes, typically making use of samples on the order of nanoliters and even picoliters. The substrates may be produced at relatively low cost, and the channels can be arranged to perform numerous specific analytical operations, including mixing, dispensing, valving, reactions, detections, electrophoresis, and the like. The analytical capabilities of such microfluidic systems may be enhanced by increasing the number and complexity of network channels, reaction chambers, and the like. However, in its simplest form for the purposes of the present invention involving linear arrays, the microfluidic system is often less complex.

The length of the linear array as manufactured may be a fixed length determined by the number of features of the linear array. The number of features is related to the nature of the features, the nature of the analytes, the complexity of the biological or clinical questions being investigated, the number of quality control features desired, and so forth. A typical linear array may contain more than about ten, more than about one hundred, more than about one thousand, more than about ten thousand, more than about twenty thousand, etc., more than about one hundred thousand, features and so forth.

The housing comprising the linear array may be prepared in a number of ways. The following discussion is by way of illustration and not limitation. In one approach, the linear array is synthesized or deposited on the surface of a housing substrate and the area comprising at least the linear array is enclosed to form a channel comprising the linear array and also a mixing area or chamber if desired. Enclosure may be attained using an appropriate material to cover the channel and then sealing to form the housing. The apparatus may be fabricated using other convenient means, including conventional molding and casting techniques, extrusion sheet forming, calendaring, thermoforming, and the like. For example, with apparatus prepared from a plastic material, a silica mold master, which is negative for the network structure in the planar substrate of one plate can be prepared by etching or laser micromachining. In addition to having a raised ridge, which forms the channel in the substrate, the silica mold may have a raised area that provides for one or more cavity structures in the planar substrate. Next, a polymer precursor formulation can be thermally cured or photopolymerized between the silica master and support planar plate, such as a glass plate.

In one embodiment, the linear array may be synthesized or deposited on the surface of a flexible material or substrate in the dimensions desired. For example, for a microarray the chemical compounds comprising the linear array are synthesized or deposited in an area that corresponds to capillary dimensions. The flexible substrate may be substantially flat along the area of synthesis or deposition or there may be a groove, depression, or the like in the housing substrate where the linear array is placed. This area of deposition or synthesis is ultimately enclosed to form a channel having the linear array therein. See, for example, U.S. patent application Ser. No. 10/037,757, entitled "Chemical Arrays" by Schembri, et al., filed Oct. 18, 2001, published as U.S. Patent Publication No. 20030108726 and U.S. patent application Ser. No. 10/032,608, entitled "Chemical Arrays", by Lefkowitz, et al., filed Oct. 18, 2001, published as U.S. Patent Publication No. 20030077380, the relevant disclosures of which are incorporated herein by reference.

Enclosing the housing to form the channel comprising the linear array and the mixing area or chamber, if one is included, may be accomplished in a number of ways. One important consideration in forming the linear array housing in general, and enclosing the housing in particular, is to avoid damage to the linear array on the surface of the housing substrate. In one approach, for example, the substrate is a flexible material that is folded over to enclose the housing to form the channel. After folding, the flexible material is sealed to itself in an area outside the area of the channel and mixing area. Sealing may be achieved by application of heat, adhesives, and so forth.

In an alternate approach, a separate material may be placed over the substrate comprising the linear array and the mixing area. The separate material is sealed to the substrate to enclose the housing to form the channel with the linear array therein and the mixing area. The separate material may be sealed to the substrate as discussed above. The separate material may have the same composition as the substrate or a composition that is different from the substrate. The separate material may be flexible or rigid.

The flexible substrate may be a plastic, that is, any synthetic organic polymer of high molecular weight (for example at least 1,000 grams/mole, or even at least 10,000 or 100,000 grams/mole. In one embodiment in accordance with the above disclosure, the flexible substrate may have a number of different layers. A base layer forms the greatest thickness and may consist of any flexible plastic such as a polyolefin film (such as polypropylene, polyethylene, polymethylpentene) or polyetheretherketone, polyimide, any of the fluorocarbon polymers or other suitable flexible thermoplastic polymer film. The material of the base layer is best selected to provide stable dimensional, mechanical, and chemical properties as well as severability. The flexible substrate may also include an optional reflective layer and a transparent layer. The reflective layer may be aluminum, silver, gold, platinum, chrome or other suitable metal film deposited by vacuum deposition, plasma enhanced chemical vapor deposition or other means onto the base layer or an optional intermediate bonding layer. Alternatively, the reflective layer may be constructed using multiple dielectric layers designed as a dielectric Bragg reflector or the like. A bonding layer, if used, may be any suitable material that is flexible at the thickness used and bonds to the base layer and/or the reflective layer. The bonding layer may have a thickness of less than about 50 nm, or even less than about 20, about 10, about 5 or about 1 nm and typically more than about 0.1 or about 0.5 nm). A glass layer (which term is used to include silica) may be deposited onto the reflective layer by sputtering, plasma enhanced chemical vapor deposition or similar techniques such as described in. A glass layer may optionally be used without a reflective layer. In the above configuration of the flexible substrate, the use of a glass layer allows the use of conventional chemistries, as discussed above, for substrate coating, feature fabrication, and array usage (for example, hybridization in the case of polynucleotide arrays). Such chemistries are well known for arrays on glass substrates, as described in the references cited herein and elsewhere. Furthermore, using a reflective layer not only can provide the useful characteristics mentioned in the above referenced patent application Ser. No. 09/493,958, but can avoid undesirable optical characteristics of the plastic base layer (for example, undesirable fluorescence, and in some instances, excessive heating and possible melting of the substrate). This allows for the ability to use base layers of a material that may have a high fluorescence and/or high absorbance of incident light. Use of a non-reflective opaque layer (for example, a suitably dyed plastic or other layer) in place of reflective layer also allows the use of the foregoing materials for a base layer although in such a case some heat may then be generated in the opaque layer.

The mechanism for causing a pressure differential on an intermittent basis to move fluid back and forth within the capillary channel and a mixing area may be any suitable mechanism. In one embodiment the mechanism is one that generates centrifugal force and may be any mechanism that can intermittently generate centrifugal force on the interior of the housing. In one embodiment the mechanism comprises a rotatable support upon which one or more of the housings are mounted. The rotatable support may be any structure that provides support for the linear arrays and that is capable of rotation about an axis, which may be a central axis. The rotatable support may be, for example, a circular tray such as a carousel or the like. The circular tray and mechanism may be similar in design to that employed, for example, in the Agilent G2505 Scanner, Agilent Technologies Inc., Palo Alto Calif.

The rotatable support may have a surface for receiving and holding the housings for the linear arrays. Thus, the surface of the rotatable support generally has a plurality of retaining elements for retaining the linear array housings on the surface. The design of the retaining elements is dependent on the nature of the housing for the linear array. The retaining elements should retain the housings sufficiently so that, during rotation of the support and other manipulations, the linear arrays remain securely on the surface. Such retaining elements include, for example, grooves in the surface of the rotatable support, elevated slots on the surface of the support, and so forth. The retaining elements may be disposed around the axis of rotation of the rotatable support. The orientation of the retaining elements should be such that the housings for the linear arrays are situated so that operation of the present apparatus to mix fluids in the channel comprising the linear array and to remove fluids from the channel as desired may be accomplished by rotation of the rotatable housing. In some circumstances, the orientation of the retaining elements, and thus the linear arrays, should also allow accurate analysis of the reaction results.

The dimensions of the rotatable support depend on the nature of the housings of the linear arrays, the required distance of the housings from the axis of rotation of the support, and so forth. The dimensions of the rotatable support should be governed by practical considerations such as the overall size of the device, the size of the motor required to rotate the support and the like. The dimensions of the rotatable support should be large enough to accommodate the number of linear arrays on its surface, but not so large as to be impractical. For linear microarrays of approximately 20 mm in length, the dimensions of the rotatable support that is circular may be about 25 mm to about by 35 mm, about 28 to 30 mm.

The housings for the linear arrays should be disposed from the axis of rotation of the rotatable support so that the linear array exit port is a sufficient distance from the axis of rotation so that fluid in the linear array may be moved through and out of the linear array. The housings for the linear array are about 5 to about 100 microns, about 10 to about 50 microns, from the axis of rotation of the rotatable support.

The number of retaining elements, and thus the maximum number of linear array housings, on the surface of the rotatable support is about 1 to about 1,000, about 5 to about 500, about 10 to about 100, about 20 to about 80.

The rotatable support is driven by a suitable driving mechanism such as a motor and the like, which is capable of rotating the rotatable support in accordance with the present invention. Accordingly, the driving mechanism is adapted to rotate the rotatable support at speeds required to mix fluids in the channel comprising the linear array and the to subsequently overcome capillary forces in the microchannels of the linear arrays. In some embodiments, it may be desirable to rotate the rotatable support in a step-wise fashion to index the linear arrays to, for example, an examining device. A motor may be, for example, a stepping-type motor, a servo-type motor, and so forth. The driving mechanism may be in communication with a system controller, which provides control over the speed of rotation of the rotatable support, indexed movement of the rotatable support, and so forth. The speed of rotation of the rotatable support is dependent on a number of factors including, for example, the nature of the function being performed at any point in time, and so forth. For removal of fluid from the interior of the linear array, the rotatable support is rotated at a speed great enough to produce a centrifugal force that overcomes the capillary forces on the fluid. This speed is dependent on the surface tension, etc., of the fluid, the capillary dimensions of the channel, the capillary dimensions of the structure, the distance of the capillary from the center of rotation, and the like. The pressures for achieving the desired results are dependent on the mechanical properties of the fluids, the mechanical properties of the surface of the capillary channel, the dimensions of the capillary, and so forth. The pressure for mixing varies from about 1 to about 100 inches of water, from about 2 to about 50 inches of water, from about 4 to about 30 inches of water. Where the pressure generated is centrifugal force, the speed of rotation of the linear array may be employed to achieve the desired effect. For mixing, the speed of rotation may be intermittently varied.

The driving mechanism may provide for indexing of the linear arrays on the surface of the rotatable support. To assist in the indexing function, the linear array housings may comprise an identification code. A suitable reading device is employed for reading the identification code. The reading device is incorporated into the present apparatus or is separate from the present apparatus. The reading device is located so as to provide an accurate reading of the identification code of the linear array housings. The code is read at a time best suited for providing accurate identification. Thus, the reading device may read the code when each of the housings for the linear arrays is in place on the rotatable support. The code may also be read while the housings are loaded onto the rotatable support. Information read from the identification code is fed to a system controller for the apparatus and correlated with the indexed position of the housing on the rotatable support. In this way the identity and location of each of the linear array housings can be tracked and the processing of each linear array may be linked to the identification code. Such information may be loaded into a data storage database for use by other systems.

Figure 1:
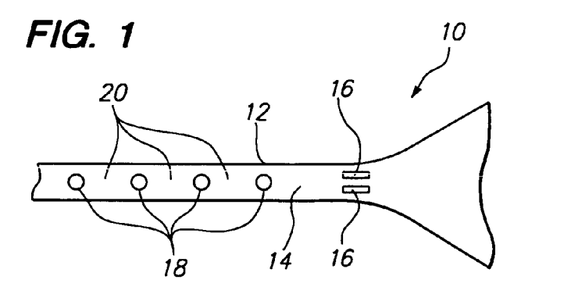
FIG. 1 is a perspective view taken from the top of a portion of an embodiment of an apparatus in accordance with the present invention.
Figure 2:
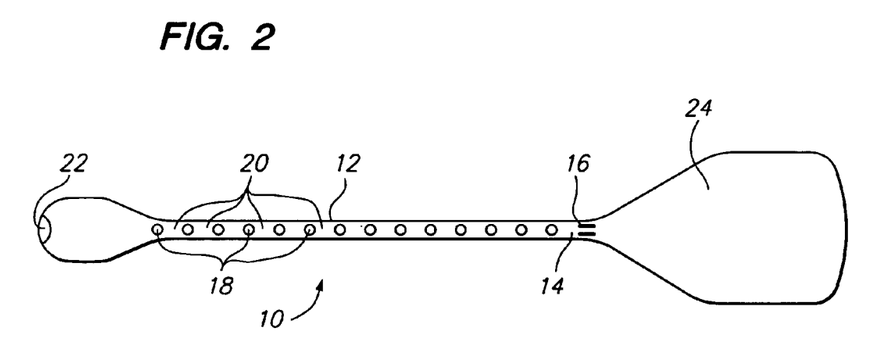
FIG. 2 is a perspective view taken from the top of a larger portion of the embodiment of FIG. 1.

An example of a specific embodiment of an apparatus in accordance with the present invention is discussed next with reference to the attached drawings. Referring to FIGS. 1 and 2, apparatus 10 is depicted and comprises housing 12 with capillary channel 14 and structural members 16 adjacent an end of channel 14. Within channel 14 are a linear array of features 18. Entry port 22 is approximate one end of housing 12 and mixing area or chamber 24 is approximate an opposing end of housing 12.

Figure 3:
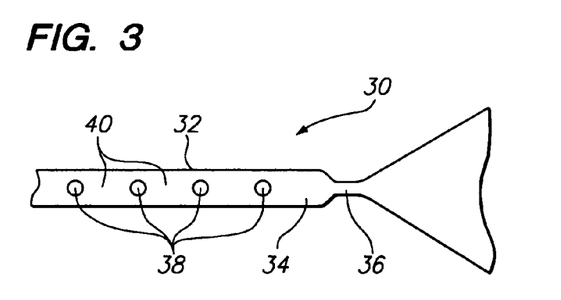
FIG. 3 is a perspective view taken from the top of a portion of another embodiment of an apparatus in accordance with the present invention.

Another example of a specific embodiment of an apparatus in accordance with the present invention is set forth in FIG. 3. Apparatus 30 is depicted and comprises housing 32 with capillary channel 34 having narrowing section 36 (or neck) as a structural member adjacent an end of channel 34. Within channel 34 are a linear array of features 38 separated by regions 40 that are free of features.

Figure 4:
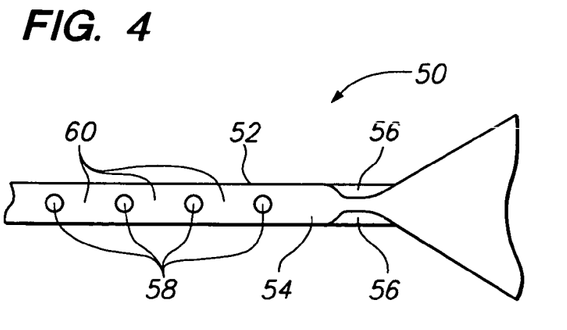
FIG. 4 is a perspective view taken from the top of a portion of another embodiment of an apparatus in accordance with the present invention.

Another example of a specific embodiment of an apparatus in accordance with the present invention is set forth in FIG. 4. Apparatus 50 is depicted and comprises housing 52 with capillary channel 54 having structural members 56 (that form a narrowing section or neck) adjacent an end of channel 54. Within channel 54 are a linear array of features 58 separated by regions 60 that are free of features.

Referring to FIGS. 1 and 2, features 18 of the linear array are non-diffusively bound an interior surface of channel 14. Inter-feature regions 20 separate features 18. A typical linear array may contain from about 100 to about 100,000 features. At least some, or all, of the features are of different compositions (for example, when any repeats of each feature composition are excluded the remaining features may account for at least about 5%, about 10%, or about 20% of the total number of features). Each feature carries a predetermined moiety (such as a particular polynucleotide sequence), or a predetermined mixture of moieties (such as a mixture of particular polynucleotides).

A linear array of features is a one-dimensional array of features bound in a non-diffusive manner to a surface. By the term "non-diffusive" is meant that the molecules that make up the individual features are bound to the surface in such a manner that they will not detach under the conditions of preparing and using the linear array. Non-diffusive binding may be covalent or may be non-covalent or macromolecular association where the linking is of sufficient strength to withstand the aforementioned conditions. Non-diffusive binding of the features may be achieved in a number of approaches known in the art. Some of those approaches are discussed briefly hereinbelow by way of illustration and not limitation.

The features generally are molecules that are involved in the detection of target molecules or analytes in a sample of interest. Each molecule of a feature may be specific for a corresponding analyte or for a compound indicative of the presence of the analyte. For example, the analyte may be part of a complex such as, for example, an antigen-antibody complex, polynucleotide-protein complex, polynucleotide-polynucleotide complex and the like, and the feature is capable of binding to a component of the complex. The molecule comprising the feature may be a specific binding partner for the analyte or for a member of the complex indicative of the presence of the analyte. The members of a pair of molecules (e.g., a detector probe or a capture probe and a target analyte, or the members of a specific binding pair (e.g., antibody-antigen, nucleic acid, and protein-vitamin binding pairs) are said to "specifically bind" to each other if they bind to each other with greater affinity than to other, non-specific molecules. For example, an antibody raised against an antigen to which it binds more efficiently than to a non-specific antigen can be described as specifically binding to the antigen. Similarly, a nucleic acid probe can be described as specifically binding to a nucleic acid target if it forms a specific duplex with the target by base pairing interactions.

Each feature, or element, within the linear array is defined to be a small, regularly shaped region of the surface of the substrate. The features in the linear array are arranged in a predetermined manner. Each feature of a linear array may carry a predetermined chemical compound or mixtures thereof. Each feature within the linear array may contain a different molecular species, and the molecular species within a given feature may differ from the molecular species within the remaining features of the molecular array. Some or all of the features may be of different compositions. Each array may be separated by spaces or areas. Interarray areas and interfeature areas may be present but are not essential. These interarray and interfeature areas do not carry any chemical compound such as polynucleotide (or other biopolymer of a type of which the features are composed). Interarray areas and interfeature areas typically will be present where arrays are formed by the conventional in situ process or by deposition of previously obtained moieties, as described herein, by depositing for each feature at least one droplet of reagent such as from a pulse jet but may not be present when, for example, photolithographic array fabrication processes are used. It will be appreciated though that the interarray areas and interfeature areas, when present, could be of various sizes and configurations.

In the linear array the order of the features identifies each feature, which allows selective identification of target molecules. The linear array may have a fixed length determined by the number of features of the linear array. The width of the linear array may be one feature. However, for purposes of the present invention, the width of the linear array may be greater than one feature where the size of the feature and the width of the housing, e.g., microchannel, permit. Therefore, the width of the linear array may be 1 to about 5 features, 1 to about 4 features, 1 to about 3 features, 1 to 2 features. In such an embodiment where the linear array is more than one feature wide, each feature comprising the width at the position in question may be the same or different and each feature comprising the length of the linear array may be the same or different, typically different, as discussed above. The width of the features, for example, the diameter of a round spot, may be in the range from about 10 μm to about 1.0 cm. In other embodiments each feature may have a width in the range of about 1.0 μm to about 1.0 mm, about 5.0 μm to about 500 µm, about 10 µm to about 200 µm. Non-round features may have width ranges equivalent to that of circular features with the foregoing width (diameter) ranges.

The interior surface of the housing to which a plurality of chemical compounds is attached to form the linear array can be hydrophilic or capable of being rendered hydrophilic or it may be hydrophobic. The interior surface is normally treated to create a primed or functionalized surface, that is, a surface that is able to support the attachment of a fully formed chemical compound or the synthetic steps involved in the production of the chemical compound on the surface of the substrate. Functionalization relates to modification of the surface of a substrate to provide a plurality of functional groups on the substrate surface. By the term "functionalized surface" is meant a substrate surface that has been modified so that a plurality of functional groups are present thereon at discrete sites on the surface. The manner of treatment is dependent on the nature of the chemical compound to be synthesized or deposited and on the nature of the surface. In one approach a reactive hydrophilic site or reactive hydrophilic group is introduced onto the surface of the substrate. Such hydrophilic moieties can be used as the starting point in a synthetic organic process.

The surface of the housing onto which the chemical compounds are deposited or formed may be modified with one or more different layers of compounds that serve to modify the properties of the surface in a desirable manner. Such modification layers, when present, will generally range in thickness from a monomolecular thickness to about 1 mm, typically from a monomolecular thickness to about 0.1 mm and more typically from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethylene amines, polyarylene sulfides, polysiloxanes, polyimides, polyacetates, and the like, where the polymers may be hetero- or homo-polymeric, and may or may not have separate functional moieties attached thereto (for example, conjugated). Various further modifications to the particular embodiments described above are, of course, possible. Accordingly, the present invention is not limited to the particular embodiments described in detail above.

As mentioned above, the chemical compounds that are bound to the interior surface of the housing to form the linear array may be synthesized or deposited on the surface. An initial derivatization of the surface may be carried out. Modification of surfaces for use in chemical synthesis has been described. See, for example, U.S. Pat. No. 5,624,711 (Sundberg), U.S. Pat. No. 5,266,222 (Willis) and U.S. Pat. No. 5,137,765 (Farnsworth).

The arrays may be microarrays created on the interior surface of the housing by in situ synthesis of biopolymers such as polynucleotides, polypeptides, polysaccharides, etc., and combinations thereof, or by deposition of molecules such as oligonucleotides, cDNA and so forth. In general, arrays are synthesized on a surface by one of any number of synthetic techniques that are known in the art.

In one embodiment, the surface of the substrate is siliceous, i.e., the surface comprises silicon oxide groups, either present in the natural state or introduced by techniques well known in the art. One technique for introducing siloxyl groups onto the surface involves reactive hydrophilic moieties on the surface. These moieties are typically epoxide groups, carboxyl groups, thiol groups, and/or substituted or unsubstituted amino groups as well as a functionality that may be used to introduce such a group such as, for example, an olefin that may be converted to a hydroxyl group by means well known in the art. One approach is disclosed in U.S. Pat. No. 5,474,796 (Brennan), the relevant portions of which are incorporated herein by reference. A siliceous surface may be used to form silyl linkages, i.e., linkages that involve silicon atoms. The silyl linkage may involve a silicon-oxygen bond, a silicon-halogen bond, a silicon-nitrogen bond, or a silicon-carbon bond.

Another method for attachment is described in U.S. Pat. No. 6,219,674 (Fulcrand, et al.). A surface is employed that comprises a linking group consisting of a first portion comprising a hydrocarbon chain, optionally substituted, and a second portion comprising an alkylene oxide or an alkylene imine wherein the alkylene is optionally substituted. One end of the first portion is attached to the surface and one end of the second portion is attached to the other end of the first portion chain by means of an amine or an oxy functionality. The second portion terminates in an amine or a hydroxy functionality. The surface is reacted with the substance to be immobilized under conditions for attachment of the substance to the surface by means of the linking group.

Another method for attachment is described in U.S. Pat. No. 6,258,454 (Lefkowitz, et al.). A solid substrate having hydrophilic moieties on its surface is treated with a derivatizing composition containing a mixture of silanes. A first silane provides the desired reduction in surface energy, while the second silane enables functionalization with molecular moieties of interest, such as small molecules, initial monomers to be used in the solid phase synthesis of oligomers, or intact oligomers. Molecular moieties of interest may be attached through cleavable sites.

A procedure for the derivatization of a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used to carry out the present methods. Such a derivatization procedure is described in EP 0 173 356 B1, the relevant portions of which are incorporated herein by reference. Other methods for treating the surface of a substrate to which the chemical compounds become bound will be suggested to those skilled in the art in view of the teaching herein.

The invention has particular application to linear arrays of oligomers or polymers. The oligomer or polymer is a chemical entity that contains a plurality of monomers. It is generally accepted that the term "oligomers" is used to refer to a species of polymers. The terms "oligomer" and "polymer" may be used interchangeably herein. Polymers comprise at least two monomers. Oligomers generally comprise about 6 to about 20,000 monomers, typically, about 10 to about 10,000, more typically about 15 to about 4,000 monomers. Examples of polymers include polydeoxyribonucleotides, polyribonucleotides, other polynucleotides that are C-glycosides of a purine or pyrimidine base, or other modified polynucleotides, polypeptides, polysaccharides, and other chemical entities that contain repeating units of like chemical structure. Exemplary of oligomers are oligonucleotides and peptides.

A monomer is a chemical entity that can be covalently linked to one or more other such entities to form an oligomer or polymer. Examples of monomers include nucleotides, amino acids, saccharides, peptoids, and the like and subunits comprising nucleotides, amino acids, saccharides, peptoids and the like. The subunits may comprise all of the same component such as, for example, all of the same nucleotide or amino acid, or the subunit may comprise different components such as, for example, different nucleotides or different amino acids. The subunits may comprise about 2 to about 2000, or about 5 to about 200, monomer units. In general, the monomers have first and second sites (e.g., C-termini and N-termini, or 5' and 3' sites) suitable for binding of other like monomers by means of standard chemical reactions (e.g., condensation, nucleophilic displacement of a leaving group, or the like), and a diverse element that distinguishes a particular monomer from a different monomer of the same type (e.g., an amino acid side chain, a nucleotide base, etc.). The initial substrate-bound, or support-bound, monomer is generally used as a building block in a multi-step synthesis procedure to form a complete ligand, such as in the synthesis of oligonucleotides, oligopeptides, oligosaccharides, etc. and the like.

A biomonomer references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A biopolymer is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

Polynucleotides are compounds or compositions that are polymeric nucleotides or nucleic acid polymers. The polynucleotide may be a natural compound or a synthetic compound. Polynucleotides include oligonucleotides and are comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. The polynucleotide can have from about 2 to 5,000,000 or more nucleotides. The oligonucleotides may be at least about 2 nucleotides, about 5 to about 100 nucleotides, about 10 to about 50 nucleotides, and may be about 15 to about 30 nucleotides, in length. Polynucleotides include single or multiple stranded configurations, where one or more of the strands may or may not be completely aligned with another.

A nucleotide refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "polynucleotide" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides.

The devices and methods of the present invention are particularly useful where the chemical compounds of the array are oligonucleotides and such oligonucleotide arrays are severed by the user and employed for determinations of polynucleotides.

As mentioned above, biopolymer arrays can be fabricated by depositing previously obtained biopolymers (such as from synthesis or natural sources) onto a substrate, or by in situ synthesis methods. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as repeating at each spot the sequence of: (a) deprotecting any previously deposited monomer so that it can now link with a subsequently deposited protected monomer; and (b) depositing a droplet of another protected monomer for linking. Different monomers may be deposited at different regions on the substrate during any one iteration so that the different regions of the completed array will have different desired biopolymer sequences. One or more intermediate further steps may be required in each iteration, such as oxidation, capping and washing steps. The deposition methods basically involve depositing biopolymers at predetermined locations on a substrate, which are suitably activated such that the biopolymers can link thereto. Biopolymers of different sequence may be deposited at different regions of the substrate to yield the completed array. Washing or other additional steps may also be used. Reagents used in typical in situ synthesis are water sensitive, and thus the presence of moisture should be eliminated or at least minimized.

The in situ method for fabricating a polynucleotide array typically follows, at each of the multiple different addresses at which features are to be formed, the same conventional iterative sequence used in forming polynucleotides from nucleoside reagents on a substrate by means of known chemistry. This iterative sequence is as follows: (a) coupling a selected nucleoside through a phosphite linkage to a functionalized substrate in the first iteration, or a nucleoside bound to the substrate (i.e. the nucleoside-modified substrate) in subsequent iterations; (b) optionally, but typically, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized substrate (in the first cycle) or deprotected coupled nucleoside (in subsequent cycles) provides a substrate bound moiety with a linking group for forming the phosphite linkage with a next nucleoside to be coupled in step (a). A number of reagents involved in the above synthetic steps such as, for example, phosphoramidite reagents, are sensitive to moisture and anhydrous conditions and solvents are employed. Final deprotection of nucleoside bases can be accomplished using alkaline conditions such as ammonium hydroxide, in a known manner.

The foregoing chemistry of the synthesis of polynucleotides is described in detail, for example, in Caruthers, *Science* 230: 281–285, 1985; Itakura, et al., *Ann. Rev. Biochem.* 53: 323–356; Hunkapillar, et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, and 5,869,643, EP 0294196, and elsewhere.

As mentioned above, various ways may be employed to produce an array of polynucleotides on the surface of a substrate. Such methods are known in the art. One in situ method employs pulse-jet technology to dispense the appropriate phosphoramidite reagents and other reagents onto individual sites on a surface of a substrate. Oligonucleotides are synthesized on a surface of a substrate in situ using phosphoramidite chemistry. Solutions containing nucleotide monomers and other reagents as necessary such as an activator, e.g., tetrazole, are applied to the surface of a substrate by means of thermal pulse-jet technology (although piezoelectric activated pulse jets might also be used, but in any event the pulse jets used must be constructed of materials chemically compatible with the solutions used). Individual droplets of reagents are applied to reactive areas on the surface using, for example, a thermal pulse-jet type nozzle. The surface of the substrate may have an alkyl bromide trichlorosilane coating to which is attached polyethylene glycol to provide terminal hydroxyl groups. These hydroxyl groups provide for linking to a terminal primary amine group on a monomeric reagent. Excess of non-reacted chemical on the surface is washed away in a subsequent step. For example, see U.S. Pat. No. 5,700,637 and PCT WO 95/25116 and PCT application WO 89/10977.

Another approach for fabricating an array of biopolymers on a substrate using a biopolymer or biomonomer fluid and using a fluid dispensing head is described in U.S. Pat. No. 6,242,266 (Schleifer, et al.). The head has at least one jet that can dispense droplets onto a surface of a substrate. The jet includes a chamber with an orifice and an ejector, which, when activated, causes a droplet to be ejected from the orifice. Multiple droplets of the biopolymer or biomonomer fluid are dispensed from the head orifice so as to form an array of droplets on the surface of the substrate.

In another embodiment (U.S. Pat. No. 6,232,072) (Fisher) a method of, and apparatus for, fabricating a biopolymer array is disclosed. Droplets of fluid carrying the biopolymer or biomonomer are deposited onto a front side of a transparent substrate. Light is directed through the substrate from the front side, back through a substrate backside and a first set of deposited droplets on the first side to an image sensor.

An example of another method for chemical array fabrication is described in U.S. Pat. No. 6,180,351 (Cattell). The method includes receiving from a remote station information on a layout of the array and an associated first identifier. A local identifier is generated corresponding to the first identifier and associated array. The local identifier is shorter in length than the corresponding first identifier. The addressable array is fabricated on the substrate in accordance with the received layout information.

The housing for the linear array may include an identifier, which is generated and used as described in U.S. Pat. No. 6,180,351 titled "Chemical Array Fabrication with Identifier". The identifiers may also optionally include a communication address, which identifies the address of a remote location on communication channel from which one or more characteristics of an array will be communicated in response to a received communication of the associated identifier. Such remote location may be that of communication module or alternatively that of another accessible memory on a communication channel carrying the database of array characteristic data and associated identifiers. Examples of a communication address may be a telephone number, computer ID on a WAN, or an internet Universal Resource Locator.

In a method for conducting chemical reactions in accordance with the present invention, a sample is introduced into a housing by capillary action wherein the chemical reactions are conducted within the housing. The sample is incubated in the housing under conditions for carrying out the chemical reactions and centrifugal force is applied to the interior of the housing to the extent necessary to cause mixing of the sample in the housing but not exit of the sample from the housing. Sample is then removed from the housing by increasing the centrifugal force applied to the interior of the housing.

An apparatus in accordance with the present invention may be employed to conduct the chemical reactions in the linear arrays. In one approach various assays involving biopolymers may be carried out. A plurality of linear array housings may be secured on the surface of a rotatable support by means of retaining elements. Typically, the linear arrays are heated to a predetermined temperature using on-board heating elements. An entry port of the housing for each of the linear arrays is exposed to a sample suspected of containing the analyte(s) of interest (for example, a fluorescent-labeled polynucleotide or protein-containing sample). The sample may be introduced manually or mechanically. For example, a user may place the sample at the entry port by suitable means such as a pipette or the like. Alternatively, a computer controlled robotic system can be employed. A computer controls the location of the application of the sample so that the sample is placed in the correct housing. An indexing system as discussed above assists in this process.

Other means of introducing the sample to the linear array include, for example, a sipper structure such as that disclosed in U.S. Patent Application Publication. No. 20030070833, entitled Extensible Spiral for Flex Circuit.

In another approach the sample movement may be controlled by an external valve such as, for example, that disclosed in U.S. Patent Application Publication No. 20030015682.

The sample may be introduced into the microchannel of the housing device through an opening that corresponds to the beginning and is moved into the microchannel by capillary action or capillary force. However, movement of the sample into the channel may also be assisted.

After the linear array has been contacted with the sample, the sample and the linear array are maintained in contact for a period of time and under conditions sufficient to achieve the desired chemical reactions. The conditions for a reaction, such as, for example, period of time of contact, temperature, pH, salt concentration and so forth, are dependent on the nature of the chemical reaction, the nature of the chemical reactants including the liquid samples, and the like. Conditions for binding of members of specific binding pairs are generally well known and will not be discussed in detail here. The conditions for the various processing steps are also known in the art.

The time and conditions depend on the nature of the chemical reactions and, generally, will be apparent to those skilled in the art in view of the disclosure herein and the knowledge of the skilled artisan. One or more incubation periods may be employed. During this incubation period, the housing is rotated intermittently at different speeds of rotation to cause reciprocal movement of the sample between the mixing area and the capillary channel. By selection of appropriate predetermined speeds of rotation, sample is mixed in the channel.

It is desirable to keep the linear array from drying. Thus, the linear array may be maintained wet at all times by contact with sample or other fluid such as wash solution and the like. In many instances residual sample and other fluids will accomplish this wetting. Drying of the linear arrays is dependent on a number of factors such as, for example, the speed at which the sample and other fluids traverse the linear array, the chemical composition of the hybridization buffer, and so forth. Ideally, the linear array surface is kept uniformly wet, i.e., the surface has a film of fluid that has uniform thickness and so forth.

After the desired incubation period(s), the sample is removed from the microchannel. The rotatable support on which the linear array housings are disposed is rotated at a speed and for a time sufficient to overcome capillary forces within the microchannel and move the sample out of the microchannel. For this purpose, the speed of rotation is about 20 to about 20,000 rpm, about 30 to about 15,000 rpm, about 50 to about 10,000 rpm, about 100 to about 5,000 rpm. The time of rotation is about 1 second to about 10 minutes, about 10 seconds to about 5 minutes rpm.

Sample may be removed through a port of the microchannel. The port may be an exit port separate from the entry port or it may be the entry port itself under certain circumstances. The port from which the sample and other fluids exit the microchannel is in fluid communication with a chamber for containing the removed materials. Desirably, the chamber is within the linear array housing. There may be one or more chambers for containing waste sample and fluids. The size of the chambers is dependent on the volume of the waste sample and fluids. The volume of the chambers should be at least sufficient to contain all of the materials directed to the chambers. Such chambers are well-known in the art and will not be discussed further.

Either following removal of the sample or in conjunction therewith, wash fluid is introduced into the microchannel in a manner similar to that for the sample itself. In one approach the wash fluid may be employed to push sample out of the microchannel. The wash fluid may be a buffer solution, and the like as is known in the art. The amount of wash fluid is dependent on the nature of the sample, the nature of the chemical reactions, the size of the microchannel, and so forth. Multiple washings may be employed. The wash fluid may be mixed in the microchannel in a manner similar to that for the sample.

The wash fluid is maintained in the microchannel for a period of time sufficient to accomplish removal of sample from the microchannel. The amount of time is dependent on the nature of the sample, the composition of the wash fluid such as wash buffer, and the like, and is about 1 second to about 10 minutes, about 10 seconds to about 5 minutes. Wash fluid is removed from the microchannel to a collection chamber in a manner similar to that discussed above for removal of the sample. Following incubation and wash steps, the linear array is examined for the results of the chemical reactions as will be discussed more fully below.

Use of an apparatus of the invention will be discussed with reference to FIGS. 1, 2 and 5. A sample is introduced into capillary channel 14 through entry port 22 by means of a pipette or the like, which may be manual or automated. As mentioned above, the interior of capillary channel 14 comprises a linear array of features 18. For purposes of this example, the linear array comprises 400 features at a spacing of 100 microns. Capillary channel 14 is 100 microns in width and 25 microns in depth. At the end of channel 14 are structural members 16 in the form of small barriers 20 microns in width and spaced 30 microns apart. To mix the sample in channel 14, pressure is increased on the inlet of the channel until a pressure is generated that is greater than that of the 100 micron by 25 micron capillary channel 14. This pressure increase may be achieved by rotating the linear array to increase the centrifugal force.

Figure 5:
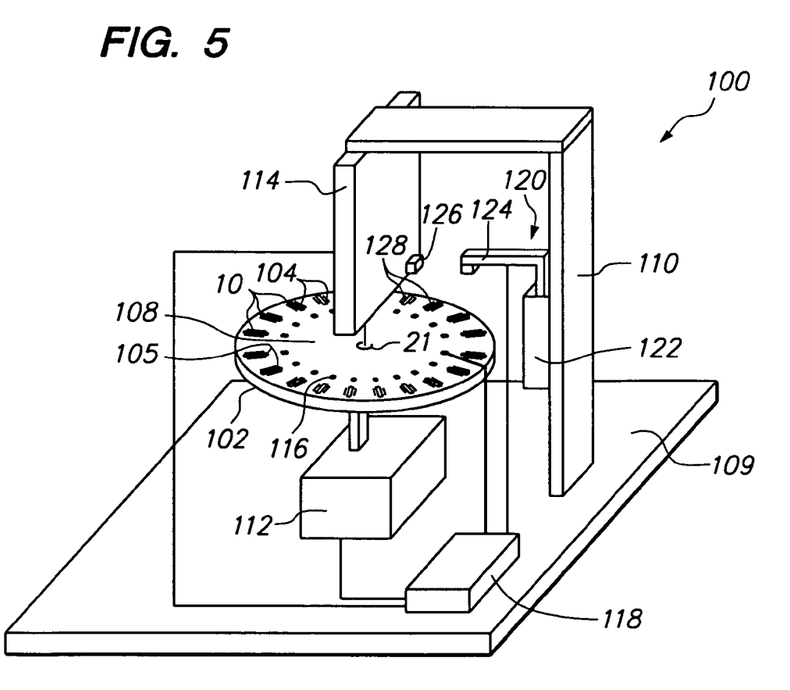
FIG. 5 is a perspective view taken from the side of an embodiment of an apparatus for rotating a plurality of linear arrays.

To this end, an apparatus such as apparatus 100 of FIG. 5 may be employed. Apparatus 100 comprises a circular tray 102 having a plurality of retaining elements 104, which retain a plurality of devices 10 on surface 108 of circular tray 102. Circular tray 102 is rotatably mounted on base member 109 of frame 110 and driven by motor 112 about axis 111. Apparatus 100 further comprises scanning device 114, which is fixedly attached to frame 110. Heaters 116 are adjacent to retaining elements 104 and communicate with computer 118, with which motor 112 and scanning device 114 also communicate. Apparatus 100 also comprises fluid dispensing device 120, which comprises fluid reservoir 122 and robotic arm 124. Fluid dispensing device 120 also communicates with computer 118. Apparatus 100 also comprises reading element 126 for reading an identifier 128 on the housing of linear arrays 16. Reading element 126 also communicates with computer 118.

For the parameters mentioned above and depending on the mechanical properties of the sample fluid and the interior surface of channel 14, the pressure generated by rotation is about 15 to about 25 inches of water or about 20 inches of water. In this way, sample is induced to move from the linear array region to mixing area or chamber 24. To return the fluid sample to the linear array, pressure is reduced and the capillary forces within channel 14 pull the sample fluid into the linear array area. This process is repeated a number of times sufficient to mix the sample. In the example above, the process is repeated about 5 to about 1000 times. To remove sample fluid from channel 14, the pressure is increased, by increasing the speed of rotation, to a level that is greater than the capillary force in channel 14. The pressure may be increased to about 1 to about 100 inches of water, about 5 to about 30 inches of water. The linear array may be washed with an appropriate wash solution in a manner similar to that described above for the mixing of sample. Wash fluid is removed also in a similar manner to that described above.

The sample in the above example is one suspected of containing the analyte(s) of interest (for example, a fluorescent-labeled polynucleotide or protein containing sample). After the linear array has been exposed to the sample and after a sufficient incubation period, the array is then read.

In general, the sample that may be analyzed in accordance with the present methods may be a trial sample, a reference sample, a combination of the foregoing, or a known mixture of components such as polynucleotides, proteins, polysaccharides and the like (in which case the arrays may be composed of features that are unknown such as polynucleotide sequences to be evaluated). The samples may be from biological assays such as in the identification of drug targets, single-nucleotide polymorphism mapping, monitoring samples from patients to track their response to treatment and/or assess the efficacy of new treatments, and so forth. For hybridization reactions the sample generally comprises a target molecule that may or may not hybridize to a surface-bound molecular probe. The term "target molecule" refers to a known or unknown molecule in a sample, which will hybridize to a molecular probe on a substrate surface if the target molecule and the molecular probe contain complementary regions. In general, the target molecule is a "biopolymer," i.e., an oligomer or polymer. The present devices and methods have particular application to various processing steps involved with the aforementioned hybridization reactions.

An oligonucleotide probe may be, or may be capable of being, labeled with a reporter group, which generates a signal, or may be, or may be capable of becoming, bound to one a feature of the linear array. Detection of signal depends upon the nature of the label or reporter group. Commonly, binding of an oligonucleotide probe to a target polynucleotide sequence is detected by means of a label incorporated into the target. Alternatively, the target polynucleotide sequence may be unlabeled and a second oligonucleotide probe may be labeled. Binding can be detected by separating the bound second oligonucleotide probe or target polynucleotide from the free second oligonucleotide probe or target polynucleotide and detecting the label. In one approach, a sandwich is formed comprised of one oligonucleotide probe, which may be labeled, the target polynucleotide and an oligonucleotide probe that is or can become bound to a surface of a support. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target polynucleotide, allowing the target polynucleotide to hybridize to a surface-bound oligonucleotide probe, washing away the unbound target polynucleotide and detecting the labeled target polynucleotide that remains. Direct detection of labeled target polynucleotide hybridized to surface-bound oligonucleotide probes is particularly advantageous in the use of ordered arrays.

In one approach, cell matter is lysed, to release its DNA as fragments, which are then separated out by electrophoresis or other means, and then tagged with a fluorescent or other label. The DNA mix is exposed to the linear array of oligonucleotide probes, whereupon selective attachment to matching probe sites takes place. The array is then washed and the result of exposure to the array is determined. In this particular example, the array is imaged by scanning the surface of the support so as to reveal for analysis and interpretation the sites where attachment occurred.

The signal referred to above may arise from any moiety that may be incorporated into a molecule such as an oligonucleotide probe for the purpose of detection. Often, a label is employed, which may be a member of a signal producing system. The label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation and (v) a specific polynucleotide sequence or recognition sequence that can act as a ligand such as for a repressor protein, wherein in the latter two instances the oligonucleotide primer or repressor protein will have, or be capable of having, a reporter molecule and so forth. The reporter molecule can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like.

The signal may be produced by a signal producing system, which is a system that generates a signal that relates to the presence or amount of a target polynucleotide in a medium. The signal producing system may have one or more components, at least one component being the label. The signal producing system includes all of the reagents required to produce a measurable signal. The signal producing system provides a signal detectable by external means, by use of electromagnetic radiation, desirably by visual examination. Signal-producing systems that may be employed in the present invention are those described more fully in U.S. Pat. Nos. 6,558,908, 6,251,588, 6,235,483 and 6,132,997, the relevant disclosure of which is incorporated herein by reference.

The section of the linear array and the liquid sample are maintained in contact for a period of time sufficient for the desired chemical reaction to occur. The conditions for a reaction, such as, for example, period of time of contact, temperature, pH, salt concentration and so forth, are dependent on the nature of the chemical reaction, the nature of the chemical reactants including the liquid samples, and the like. The conditions for binding of members of specific binding pairs are generally well known and will not be discussed in detail here. The conditions for the various processing steps are also known in the art.

The linear arrays prepared as described above are particularly suitable for conducting hybridization reactions. Such reactions are carried out on a substrate or support comprising a plurality of features relating to the hybridization reactions. The substrate is exposed to liquid samples and to other reagents for carrying out the hybridization reactions. The support surface exposed to the sample is incubated under conditions suitable for hybridization reactions to occur.

After the appropriate period of time of contact between the liquid sample and the linear array, the contact is discontinued and various processing steps are performed. Following the processing step(s), the section of the linear array is moved to an examining device where the linear array is interrogated. The examining device may be a scanning device involving an optical system.

Reading of the array may be accomplished by illuminating the array and reading the location and intensity of resulting fluorescence at each feature of the array. For example, a scanner may be used for this purpose where the scanner may be similar to, for example, the AGILENT MICROARRAY SCANNER available from Agilent Technologies Inc, Palo Alto, Calif. Other suitable apparatus and methods are described in U.S. patent application Ser. No. 09/846,125 "Reading Multi-Featured Arrays" by Dorsel, et al.; and U.S. Pat. No. 6,406,849. The relevant portions of these references are incorporated herein by reference. However, arrays may be read by methods or apparatus other than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,221,583 and 6,251,685, and elsewhere). In addition, an apparatus according to FIG. 3 may be employed to scan the linear arrays.

Results from the reading may be raw results (such as fluorescence intensity readings for each feature in one or more color channels) or may be processed results such as obtained by rejecting a reading for a feature that is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

When one item is indicated as being "remote" from another, this means that the two items are at least in different buildings and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

All publications and patent applications cited in this specification are herein incorporated by reference as if each individual publication or patent application were specifically and individually indicated to be incorporated by reference, except insofar as they may conflict with those of the present application (in which case the present application prevails). Methods recited herein may be carried out in any order of the recited events, which is logically possible, as well as the recited order of events.

The aforementioned description includes theories and mechanisms by which the invention is thought to work. It should be noted, however, that such proposed theories and mechanisms are not required and the scope of the present invention should not be limited by any particular theory and/or mechanism.

Although embodiments of the foregoing invention have been described in some detail by way of illustration and example for purposes of clarity of understanding, it will be readily apparent to those of ordinary skill in the art in light of the teachings of this invention that changes and modifications may be made thereto without departing from the spirit or scope of the appended claims. Furthermore, the foregoing description, for purposes of explanation, used specific nomenclature to provide a thorough understanding of the invention. However, it will be appreciated that one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for mixing a fluid, said method comprising:
   (a) introducing a fluid into a housing of an apparatus, said apparatus comprising:
      (i) a housing having an interior comprising an interior channel with capillary dimensions, said interior channel comprising a plurality of biopolymer features arranged in a predetermined manner on an interior surface thereof,
      (ii) an opening at a proximal end of said interior channel,
      (iii) a chamber at a distal end of said interior channel,
      (iv) a structural member in said interior channel adjacent said distal end, the dimensions of and placement of said structural member being sufficient such that intermittent application of centrifugal force to said interior channel causes movement of said fluid between said interior channel and said chamber, and
      (v) a mechanism that intermittently generates centrifugal force on the interior of said housing to cause movement of said fluid in said channel, and
   (b) generating intermittent centrifugal force to cause repetitive movement of said fluid between said interior channel and said chamber sufficient to cause mixing of said fluid by agitation.

2. A method according to claim 1 wherein said intermittent centrifugal force is generated by rotating said mechanism.

3. A method according to claim 1 wherein said interior channel comprises a linear array of biopolymer features.

4. A method according to claim 3 wherein said linear array is a linear microarray.

5. A method according to claim 4 wherein said linear microarray comprises more than one thousand features.

6. A method according to claim 1 wherein said biopolymer features are polynucleotides or polypeptides.

7. A method according to claim 1 wherein said method is a method for conducting hybridization reactions.

8. A method for conducting chemical reactions, said method comprising:
   (a) introducing a fluid sample into a housing of an apparatus, said apparatus comprising:
      (i) a housing having an interior comprising an interior channel with capillary dimensions, said interior channel comprising a linear array of biopolymer features arranged in a predetermined manner on an interior surface thereof,
      (ii) an opening at a proximal end of said interior channel,
      (iii) a chamber at a distal end of said interior channel,
      (iv) a structural member in said interior channel adjacent said distal end, the dimensions of and placement of said structural member being sufficient such that intermittent application of centrifugal force to said interior channel causes movement of said fluid between said interior channel and said chamber, and
      (v) a mechanism that intermittently generates centrifugal force on the interior of said housing to cause movement of said fluid in said channel, and
   (b) incubating said fluid sample in said housing under conditions for carrying out said chemical reactions and during said incubation generating intermittent centrifugal force to cause repetitive movement of said fluid sample between said linear array and said chamber sufficient to cause mixing of said fluid sample by agitation.

9. A method according to claim 8 wherein said intermittent centrifugal force is generated by rotating said housing.

10. A method according to claim 8 wherein said linear array is a linear microarray.

11. A method according to claim 10 wherein said linear microarray comprises more than one thousand features.

12. A method according to claim 8 wherein said biopolymer features are polynucleotides or polypeptides.

13. A method according to claim 8 wherein said method is a method for conducting hybridization reactions.

14. A method for conducting hybridization reactions, said method comprising:
   (a) introducing a fluid sample into an opening at a proximal end of a housing comprising a linear microarray of biopolymer features for hybridizing to analytes in said sample, said housing having an interior with internal capillary dimensions, a mixing area separate from said linear array at a distal end of said housing and a structural member in said housing adjacent said distal end, the dimensions of and placement of said structural member being sufficient such that intermittent application of centrifugal force to said housing causes motion of said fluid therein, and
   (b) incubating said fluid sample in said housing under conditions for carrying out said hybridization reactions and during said incubation generating intermittent centrifugal force to cause repetitive reciprocal movement of said fluid sample between said linear array and said mixing area such that said fluid sample is mixed by agitation.

15. A method according to claim 14 wherein said intermittent centrifugal force is generated by rotating said housing.

16. A method according to claim 14 further comprising, subsequent to said incubation, increasing said centrifugal force sufficient to cause said fluid to exit said interior.

17. A method according to claim 16 further comprising introducing a wash fluid into said housing and generating intermittent centrifugal force sufficient to cause agitation of said wash fluid but insufficient to cause said wash fluid to exit said housing.

18. A method according to claim 17 further comprising increasing said centrifugal force sufficient to cause said fluid to exit said interior.

19. A method according to claim 14 further comprising examining said linear array for the results of said hybridization reactions.

20. A method according to claim 19 comprising forwarding data representing a result obtained from said examining.

21. A method according to claim 20 wherein the data is transmitted to a remote location.

22. A method according to claim 19 comprising receiving data representing a result of an interrogation obtained by said examining.

23. A method according to claim 14 wherein said housing is part of a microfluidic system.

24. A method according to claim 14 wherein said housing is a channel in a microfluidic system.

25. A method according to claim 14 wherein said features are polynucleotides or polypeptides.

26. A method according to claim 14 wherein said linear microarray comprises more than one thousand features.

* * * * *